United States Patent [19]

Siposs

[11] 4,131,431
[45] Dec. 26, 1978

[54] BLOOD SHUT-OFF VALVE

[76] Inventor: George G. Siposs, 2855 Velasco La., Costa Mesa, Calif. 92626

[21] Appl. No.: 754,345

[22] Filed: Dec. 27, 1976

[51] Int. Cl.² ............................................. A61M 1/03
[52] U.S. Cl. .................. 422/45; 128/214 C; 128/214 D; 422/47
[58] Field of Search .................. 23/258.5 R, 258.5 A, 23/258.5 B, 258.5 BH; 128/214 C, 214 D, DIG. 3; 137/533.11, 533.13, 533.17, 399, 192

[56] References Cited

U.S. PATENT DOCUMENTS

| | | | |
|---|---|---|---|
| 2,018,769 | 10/1935 | Tryon | 137/533.15 X |
| 2,796,883 | 6/1957 | Thompson | 137/399 |
| 2,817,689 | 12/1957 | White | 137/192 X |
| 3,491,790 | 1/1970 | Sanford | 137/533.15 |
| 3,513,845 | 5/1970 | Chesnat | 23/258.5 B |
| 3,717,174 | 2/1973 | De Wall | 23/258.5 A X |
| 3,898,045 | 8/1975 | Bowley | 23/258.5 BH |
| 3,929,157 | 12/1975 | Serur | 128/214 C X |
| 3,993,067 | 11/1976 | Schachet | 128/214 C |
| 4,000,738 | 1/1977 | Howell | 128/214 D |

Primary Examiner—Morris O. Wolk
Assistant Examiner—Michael S. Marcus
Attorney, Agent, or Firm—Allen A. Dicke, Jr.

[57] ABSTRACT

Blood shut-off valve is positioned at the outlet of a blood oxygenator arterial reservoir so that the valve closes when the reservoir is emptied to prevent flow. Valve has a member which floats in the blood and an outlet valve seat against which the member rests in the absence of blood, together with a constraint which positions the member near the seat, but protects it from hemodynamic closing forces.

10 Claims, 5 Drawing Figures

U.S. Patent  Dec. 26, 1978  4,131,431
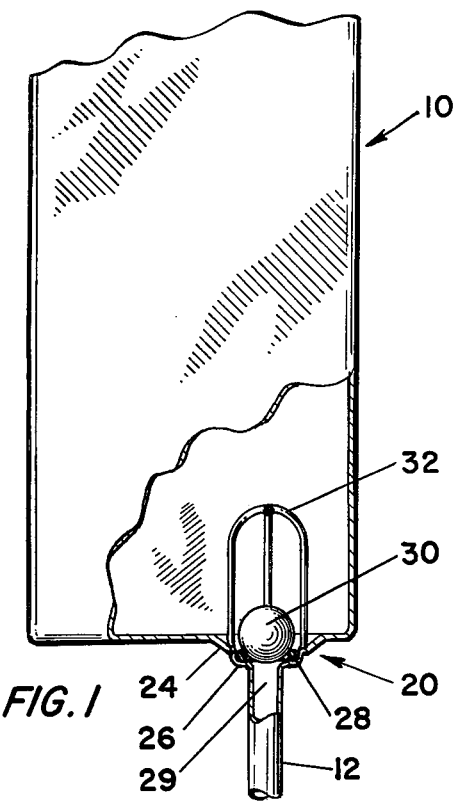
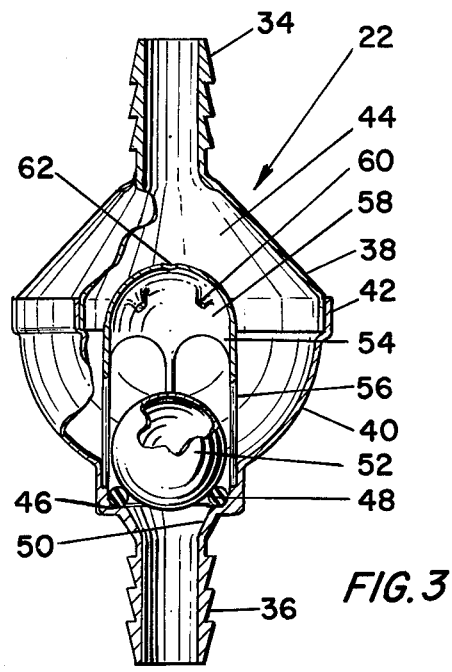
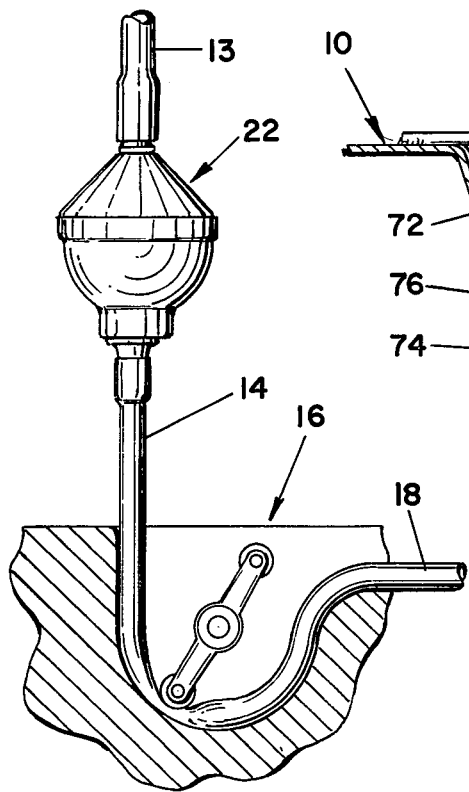
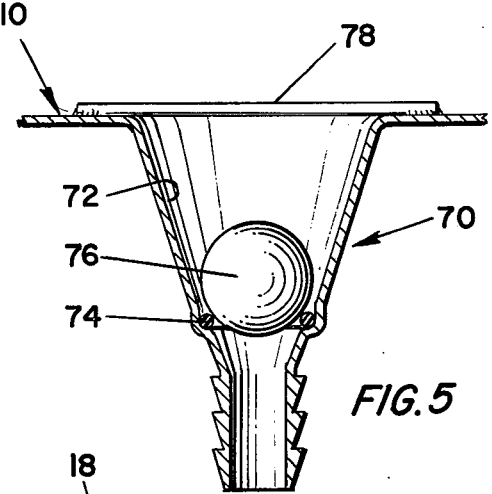
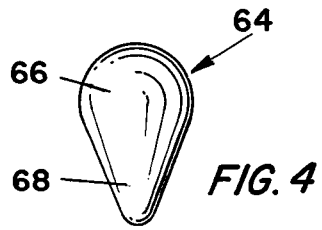

BLOOD SHUT-OFF VALVE

BACKGROUND

This invention is directed to a blood shut-off valve particularly for use in the outlet of heart-lung oxygenator equipment to automtically close the outlet line when the arterial reservoir is empty.

In an increasing number of surgical procedures, particularly in heart surgery, heart-lung oxygenators are used in an extra-corporeal circuit to maintain corporeal blood circulating during the procedure. Such oxygenators may include an oxygenation section in which oxygen is bubbled through the blood stream. Next is a defoaming section which separates the gas entrained from the liquid blood. Finally the blood is collected in an arterial reservoir at the outlet of the oxygenator.

From the outlet of the arterial reservoir, the blood flows gravitationally to the inlet of a peristaltic pump which delivers the arterial blood to the patient. Should the arterial flow reservoir in the oxygenator run dry, the arterial peristaltic pump would pump air into the patient, and death occurs almost instantaneously. It is thus necessary to shut off flow before the air is delivered to the patient.

SUMMARY

In order to aid in the understanding of this invention, it can be stated in essentially summary form that it is directed to a blood shut-off valve. The blood shut-off valve comprises a valve seat positioned in a blood flow structure. A buoyant valve member is positioned upstream from the seat so that, when the blood flow structure empties of blood, the valve member moves to its seat and closes arterial flow. The valve member is constrained adjacent the seat for quick and accurate closing.

It is thus an object of this invention to provide a blood shut-off valve which can function in the arterial blood flow downstream from the arterial reservoir of a heart-lung oxygenator to a patient. It is a further object to provide a blood shut-off valve which includes a buoyant valve member positioned between the arterial reservoir and the arterial pump to shut off flow to the arterial pump when the arterial reservoir is drained. It is a further object to provide a blood shut-off valve which has a valve member of buoyant nature which rises due to buoyancy and assumes a position which does not hinder arterial blood flow until the liquid level drops and the valve member moves toward its seat, thereby closing it to prevent flow.

Other objects and advantages of this invention will become apparent from the study of the following portion of the specification, the claims, and the attached drawings.

BRIEF DESCRIPTION OF THE DRAWINGS

FIG. 1 is a side-elevational view, with parts broken away and parts taken in section, of the outlet reservoir of a blood oxygenator showing the blood shut-off valve of this invention integrated as part of the outlet from the reservoir.

FIG. 2 is a side-elevational view, with parts broken away, showing another embodiment of the blood shut-off valve of this invention in the arterial blood line between the reservoir and the arterial blood pump.

FIG. 3 is an enlarged side-elevational view of the blood shut-off valve of FIG. 2, with parts broken away and parts taken in section.

FIG. 4 is a side-elevational view of an alternate valve member which can be alternately employed in the blood shut-off valve of FIG. 1 or FIG. 3.

FIG. 5 is a section through the outlet of a reservoir with parts broken away, showing another preferred embodiment of the blood shut-off valve of this invention.

DESCRIPTION OF THE PREFERRED EMBODIMENT

The arterial blood supply reservoir for perfusion of arterial blood for extra-corporeal supply of blood in certain surgical procedures is partly illustrated in FIGS. 1 and 2. In FIG. 1, reservoir 10 is the arterial blood reservoir at the outlet of the heart-lung oxygenator. It supplies blood for perfusion through outlet line 12 to section line 14 of peristaltic arterial pump 16. Pump 16, in turn, delivers arterial blood to the patient through outlet line 18. It is readily seen that, in normal operation, perfusion continues with the system full of blood. Of course, there are blood losses during the surgical procedure, and the reservoir 10 may well lose some of its reservoir blood. This is sometimes made up by addition of outside blood or plasma to the reservoir. Should the reservoir run dry while the perfusionist is observing or adjusting another portion of the system, a complete loss of blood in the reservoir will cause pumping of air to the patient, with almost instantaneous death. It is for these occasions and to prevent such undesirable system operating parameters that the blood shut-off valve of this invention is employed. The blood shut-off valve may either be installed as an integral structure in the outlet of reservoir 10, as illustrated in FIG. 1 by valve 20 or FIG. 5 by valve 70, or may be installed in the arterial blood supply line between reservoir 10 and arterial pump 16, as illustrated by valve 22.

Referring first to valve 20 and FIG. 1, recess 24 is formed downwardly in the bottom of the reservoir at the outlet. Step 26 is formed in recess 24, and O-ring valve seat 28 is positioned in the step. The step is of sufficient size that the O-ring is positioned substantially in line with the conical interior surface of recess 24 so that valve member 30 can roll right down the interior recess 24 without hanging up on O-ring valve seat 28. Valve member 30 is in the form of a spherical ball and is buoyant in blood. Either O-ring 28 or ball 30 is resilient so that proper valve seating action takes place when the ball is on its seat.

Cage 32 constrains the ball. Cage 32 is in the form of round members mounted to the bottom of the reservoir immediately at the edges of recess 24. The cage legs extend upward and across the top to constrain the buoyant valve ball 30. Of course, the opening between the legs is close enough to prevent egress of the ball from the inside of the cage. Thus, the valve member float 30 is constrained adjacent the outlet opening 29 by the interior opening of the O-ring valve seat. Cage 32 is sufficiently large so that valve member ball 30 can float away from the valve seat by the buoyant hemostatic force and be sufficiently far away from valve seat 28 that hemodynamic forces of blood flow toward the valve does not overcome the hemostatic buoyancy. For this reason, the bottom of reservoir 10 must be opened on the sides to the outlet, and cage 32 must be sufficiently high to remove ball 30 away from the valve seat to be away from the maximum hemodynamic forces. However, whenever the blood level in the reservoir decreases as perfusion is carried out, float ball 30 falls by gravity with the decreasing blood level and automatically sinks onto its seat being guided by the cage. This seals off the outlet and stops the flow of blood and air into line 12. Pump 16 attempts to draw blood, but pump suction line 14 collapses to change the sound of arterial pump 16. This sound warns the perfusionist that blood pumping has stopped and allows him to make the necessary system corrections, such as the addition of more blood to the extra-corporeal blood circuit.

Either alternatively to or in addition to valve 20, valve 22 may be employed in the line. Line 13 is the same as outlet line 12, with valve 22 connected between inlet line 13 and pump suction line 14. As seen in FIG. 4, valve 22 has inlet barbed fitting 34 and outlet barbed fitting 36, both of which fit the standard ⅜ inch flexible tubing used in perfusion systems. Valve 22 is formed of shell 38 and shell 40 to which are respectively secured the inlet and outlet fittings 34 and 36. The shells are secured together by overlapping seal joint 42 where they are permanently secured together and sealed together, as by adhesive. The shells and the fittings are made of a sterilizable, blood compatible preferably injection-moldable synthetic polymer composition material. Both of the shells are divergent from their fitting to the joint seal rim 42 to thus define an interior volume 44. The divergent shells are shaped to provide for smooth flow, and in the preferred embodiment shown, shell 38 is conical, while shell 40 is hemispherical. Bottom shell 40 is rounded to slow the rate of drop of blood level with respect to blood volume to provide the maximum time for ball 52 to react to falling blood level. The shells may be formed of sheet material, as by vacuum forming with the inlet and outlet fittings respectively injection-molded and secured by adhesive attachment. In any event, a closed valve body of minimized volume is provided.

Step 46 is formed in the outlet structure of the valve body. O-ring 48 is positioned in the step and serves as a valve seat. A rounded smooth transition zone 50 is provided below step 46 between the step and the bore of outlet fitting 36 in order to minimize turbulence and provide for maximum flow.

Ball 52 is a valve member which engages on O-ring 48 to close the valve. Either the valve member or the O-ring seat is resilient in order to provide full sealing. Ball valve member 52 is buoyant in blood so that, in the absence of hemodynamic forces, hemostatic force causes the ball to rise away from the seat in the presence of blood. Ball 52 can be buoyant in blood either by being made of a lower density material, or it may be hollow, as is illustrated. Thus, in the presence of blood, the valve member rises due to buoyancy and assumes a position so that downstream flow is unhindered until the liquid level drops, and then the ball (due to gravity) falls to the valve seat and seals it, preventing flow in the downstream direction. In addition to this hydrostatic buoyancy force on the ball, there may be hemodynamic forces which tend to cause it to move toward the lower outlet and thus toward the closed position. As long as the hemostatic forces are greater than the hemodynamic valve closing forces, the valve stays open until the blood level drops. However, in order to avoid relying upon the balance of forces, umbrella 54 is provided over the valve seat and around the ball. Umbrella 54 has four round legs 56 which are secured at their bottom ends adjacent the O-ring valve seat and carry umbrella 58 at their upper ends. Umbrella 58 receives the ball into its concave interior surface, which protects the ball against hemodynamic forces, as long as the valve is full of blood. In normal flow, the eddy currents due to the umbrella operate on the bottom of the ball to apply upward dynamic forces.

Projection pins 60, of which there are at least one, project downward in the upper interior of the umbrella to hold the ball away from the interior umbrella surface. This prevents the ball from sticking in place by not having an adequate place for fluid between the ball and the interior of the umbrella. Opening 66 in the top of the umbrella permits flow through the umbrella in order to let air into the umbrella as blood level falls. The hole is small enough to prevent dynamic force of blood through the hole from pushing the ball down, but communicates air as soon as it is present to let the ball fall with dropping blood level. Thus, declining blood levels are immediately communicated to valve member ball 52 as it descends inside of umbrella 54 between legs 56. The result is that ball 52 rapidly closes the outlet to stop flow. With the line closed, no more blood or air is supplied to pump 16, and its tubing (if soft enough) collapses so that the occluded line makes a different pump sound which warns the perfusionist. In this way, the patient is protected.

FIG. 4 illustrates valve member 64 which can be substituted for valve member 30 or valve member 52. It is spherical in its upper portion and conical in its lower portion 68. The lower portion serves as a tail which extends downward into the flow stream adjacent the O-ring valve seat. Valve member 64 is buoyant in blood, preferably by being hollow, and it seats on the O-ring valve seat. The height of the case is less critical when valve member 64 is used. The tail-like lower portion 68 must extend downward into the outlet, at least as far as the O-ring valve seat, to serve as a guide.

FIG. 5 shows another embodiment of the blood valve wherein it is integrally formed in the bottom of a blood reservoir, as is the structure of FIG. 1. In valve 70 of FIG. 5, conical recess 72 forms the blood volume space of the valve. Seat ring 74 has its step formed at the bottom of the cone. The walls of the cone act as constraint on buoyant valve ball 76. Cage 78 across the top of the ball volume space prevents escape of the ball.

Restraint of the valve member may include a pivoted lever which constrains a blood-buoyant valve member adjacent its seat to guide the valve member down onto its seat as blood level lowers.

This invention having been described in its preferred embodiment, it is clear that it is susceptible to numerous modifications and embodiments within the ability of those skilled in the art and without the exercise of the invention faculty. Accordingly, the scope of this invention is defined by the scope of the following claims.

What is claimed is:

1. A heart-lung oxygenator, said oxygenator having a reservoir and said reservoir having a blood outlet at the bottom of said reservoir;

a blood shutoff valve positioned at the outlet of said reservoir so that said blood shutoff valve can close when blood level falls in said reservoir, said valve comprising:

a valve body for connection into an extra-corporeal blood circuit, said valve body including an inlet, an outlet tube and an outlet member, said outlet member having a step therein;

a valve seat, said seat comprising an O-ring positioned in said step, said O-ring having an interior opening through which blood can flow to said outlet tube;

a valve member adapted to move from a position on said valve seat where it closes said valve to a position above said valve seat where it leaves said valve seat open for blood flow therethrough, said valve member being buoyant in blood so that in a fully charged system in the presence of blood, hemostatic force urges said valve member away from said valve seat to permit passage of blood downward through said outlet; and restraining means secured to said outlet means and positioned near said valve seat, said restraining means comprising a cage which has legs secured to said outlet member with said legs extending upwardly away from said outlet member, said cage comprising an umbrella secured to said upright legs adjacent to the top thereof to restrain said ball in the vicinity of said outlet member, said umbrella being shaped to protect said ball against hemodynamic force which may cause closing, said umbrella engaging said valve member to retain said valve member in a position adjacent to said valve seat so that a lowering of blood level causes said valve member to move towards said valve seat and close said valve seat as blood level descends to said valve seat, said O-ring being in its recess so that said valve member can move onto said O-ring seat without delay or obstruction.

2. The blood shut-off valve of claim 1 wherein said valve member is a sphere.

3. The blood shut-off valve of claim 1 wherein said valve member is partially spherical and partially conical with said conical portion forming a tail and said tail is positioned downward in said outlet member through said O-ring when said valve is closed.

4. The blood shut-off valve of claim 1 wherein said umbrella has a protective inner space into which said valve member rises due to hemostatic forces and said umbrella engages over and protects the top portion of said valve member against force of inflowing liquid when said valve member is in its upper buoyant position and provides eddy effect counter force.

5. The blood shut-off valve of claim 4 wherein said umbrella has an opening in the top thereof to admit blood flow and has projections therein to engage against said valve member to maintain a blood flow space through said umbrella opening and above said valve member so that said valve member remains responsive to falling blood level.

6. A heart-lung oxygenator having a reservoir and having a blood outlet body at the bottom of said reservoir with the body open to the reservoir to receive blood therefrom and a blood shutoff valve positioned at said outlet body of said reservoir so that said blood shutoff valve closes when blood level falls in said reservoir, said blood shutoff valve comprising:

an outlet on said body for connection into an extra-corporeal blood circuit;

a valve seat in said body, said valve seat having an interior opening through which blood can flow through said body to said outlet;

a valve member for moving from a position on said valve seat where it closes said valve and prevents blood flow from said reservoir to a position above said valve seat where it leaves said valve seat open for blood flow therethrough, said valve member being buoyant in blood so that in a fully charged system in the presence of blood, hemostatic force urges said valve member away from said valve seat to permit passage of blood downward out of the bottom of said reservoir and through said outlet of said blood shutoff valve; and restraining means secured adjacent said outlet and positioned near said valve seat and engaging said valve member to retain said valve member in a position adjacent said valve seat, said restraining means comprising an umbrella cage having legs secured to said outlet member around the outlet in said outlet member and engaging around said valve member, said valve member being a ball and said umbrella being shaped to engage around said ball and protect said ball against hemodynamic forces which may urge said ball valve member toward closing, said umbrella having a protective inner space into which said ball rises due to hemostatic forces and said umbrella engages over and protects the top of said valve member against the force of inflowing liquid when said ball valve member is in its upper buoyant position so that downflowing liquid provides eddy effect ball valve member counterforce to aid in holding the valve into open position so that said ball valve member moves to its seat and closes outflow only when blood level falls in the outlet of said reservoir.

7. The blood shutoff valve of claim 6 wherein said umbrella has an opening in the top thereof to admit blood flow and has projections therein to engage against said valve member to maintain a blood flow space through said umbrella opening and above said valve member so that said valve member remains responsive to falling blood level and prevents said valve member from sticking to the inside surface of said umbrella.

8. A blood shutoff valve for positioning in an extra-corporeal blood profusion system comprising:

inlet means and outlet means for connection into an extra-corporeal blood circuit;

a valve body interconnecting said inlet means and said outlet means;

a valve seat in said valve body connected to said outlet means, said valve seat having an interior opening through which blood can flow to said outlet means;

a valve member for moving from a position on said valve seat where it closes said valve and prevents blood flow from said reservoir to a position above said valve seat where it leaves said valve seat open for blood flow therethrough, said valve member being buoyant in blood so that, when said valve body is full of blood, hemostatic force urges said valve member away from said valve seat to permit passage of blood from said inlet means and out of said outlet means of said blood shutoff valve, said valve member being a ball; and restraining means secured adjacent said outlet positioned near said valve seat and engaging said valve member to retain said valve member in a position adjacent said valve seat, said restraining means comprising an umbrella cage having legs secured to said outlet member around the outlet in said outlet member and engaging around said valve member, said umbrella cage being shaped to engage around said ball-shaped valve member to protect said ball-shaped valve member against hemodynamic forces which may urge said valve ball member toward closing, said umbrella-shaped restraining means having a protected inner space into which said ball valve member rises due to hemostatic forces and said umbrella-shaped restraining means engages over and protects the top of said valve member against the force of inflowing liquid when said ball valve member is in its upper buoyant position so that downflowing liquid provides eddy effect ball valve member restraining counter-force to aid in holding the ball-shaped valve member in open position so that said ball-shaped valve member moves to its seat and closes outflow only when blood level falls in the outlet of said reservoir.

9. The blood shutoff valve of claim 8 wherein said umbrella has an opening in the top thereof to admit blood flow and has projections therein to engage against said valve member to maintain a blood flow space through said umbrella opening and above said valve member so that said valve member remains responsive to falling blood level and prevents said valve member from sticking to the inside surface of said umbrella.

10. The blood shutoff valve of claim 8 wherein said body has a wall therein with a smaller diameter toward said outlet means and there is a step recess in said wall, said valve seat comprising an O-ring positioned in said step recess, said step recess and said O-ring being dimensioned so that said O-ring does does not produce a step which could cause said ball-shaped valve member from seating.

* * * * *